United States Patent [19]
Liu et al.

[11] Patent Number: 6,040,584
[45] Date of Patent: Mar. 21, 2000

[54] METHOD AND FOR SYSTEM FOR DETECTING DAMAGED BILLS

[75] Inventors: Jiancheng Liu; Kazuo Yamazaki, both of Davis, Calif.

[73] Assignee: MTI Corporation, Aurora, Ill.

[21] Appl. No.: 09/083,138

[22] Filed: May 22, 1998

[51] Int. Cl.[7] .................................................. G01N 21/86
[52] U.S. Cl. ........................ 250/559.11; 250/559.06; 194/207; 209/534; 382/135
[58] Field of Search .......................... 209/534; 194/206, 194/207; 250/559.11, 559.04, 559.06; 382/135; 356/429, 430, 431

[56] References Cited

U.S. PATENT DOCUMENTS

| | | | |
|---|---|---|---|
| 4,255,057 | 3/1981 | Williams | 356/435 |
| 4,592,090 | 5/1986 | Curl et al. | 382/135 |
| 4,710,963 | 12/1987 | Chapman et al. | 382/112 |
| 5,955,741 | 9/1999 | Kayani | 250/559.11 |

*Primary Examiner*—Edward P. Westin
*Assistant Examiner*—Glen T Kinnear
*Attorney, Agent, or Firm*—Oliff & Berridge, PLC

[57] ABSTRACT

A method and system for determining the extent of deterioration of a bill includes generating transmitted and reflected light images. The reflected and transmitted light intensities of the transmission and reflection light intensity images are used to determine one or more disorder curve lengths for each image of the bill. Each disorder curve length is compared with a corresponding predetermined disorder curve length for a corresponding image of a reference bill to generate an evaluation factor. The positions of the evaluation factors on an evaluation map indicate the extent of deterioration of the bill.

8 Claims, 17 Drawing Sheets

$L_D > L_R$

METHOD AND FOR SYSTEM FOR DETECTING DAMAGED BILLS

BACKGROUND OF THE INVENTION

1. Field of Invention

This invention relates to a method for detecting damaged currency. In particular, the invention relates to a method that detects a degree of deterioration of damages bills or paper money.

2. Description of Related Art

It is well known that paper money is a popular form of consideration that is exchanged for goods and/or services. Individual pieces of paper money are commonly referred to as bills. As time progresses, a bill in circulation is vulnerable to various types of damage. For example, a bill can become dirty, torn, worn-down and/or wrinkled. In addition, over time, the print design on the bill gradually fades and the print ink wears off.

Typically, a consumer will tender paper money to a cashier or the like as a form of payment when purchasing an item. However, recently there has been a trend where consumers can avoid waiting in cashier lines and interact directly with a kiosk having an automatic bill-handling machine to carry out the transaction. Unfortunately, damaged bills jam the automatic bill handling machines, causing the machines to stop working. Accordingly, because removing the jammed bill from the automatic bill handling machine requires a substantial amount of time, reducing jamming occurrences has become an important problem that bill-handling machine manufacturers have been trying to solve.

Globally, the recognition of damaged bills is an important problem for banks so that the damaged bills can be identified and removed from circulation.

Because the need for a method of detecting damaged bills is widespread, a number of conventional methods for detecting damaged bills have been developed. An example of a known method preferred by some bill handling machine manufacturers uses an ultrasonic wave method to identify and separate the damaged bills from undamaged bills. However, the ultrasonic wave method is only suitable for "soft" bills, such as a very fatigued or worn-out bill.

A majority of the remainder of these conventional methods discriminate damaged bills from undamaged bills using non-contact optical methods. One non-contact optical method recognizes whether a bill in circulation, i.e., a test bill, is a damaged bill or an undamaged bill by detecting a reflected light intensity and a transmitted light intensity for the test bill when the test bill is illuminated and scanned. This non-contact optical method then determines an evaluation value from the detected reflected and transmitted light intensities of the test bill. The evaluation value for the test bill is then compared to corresponding pre-determined evaluation values obtained for a normal or reference bill to see if the evaluation value of the test bill falls within established statistical parameters for an acceptable bill. If the evaluation value for the test bill falls within the established statistical parameters, the test bill will be accepted by the bill handling machine. If the evaluation value for the test bill falls outside of the established statistical parameters, the test bill is determined to be a damaged bill and is not accepted by the bill handling machine.

SUMMARY OF THE INVENTION

However, the accuracy of the measured reflected and transmitted light intensities can be affected by many factors. One such factor known to affect the accuracy of the measured reflected and transmitted light intensities is the bill's position when the bill passes a sensor device of the automated bill handling machine. Because bills are often conveyed through the automated bill handling machine at high speeds and there are many different ways a bill may be damaged, the measured reflected and transmitted light intensities of a test bill may be difficult to differentiate from the reference reflected and transmitted light intensities of the reference bill.

Therefore, accurately and practically determining whether a test bill is damaged or not remains a problem when using this conventional non-contact optical method.

This invention provides a method and system that accurately determines whether a bill in circulation, i.e., a test bill, is a damaged bill.

This invention further provides a method and system that cost-effectively determines whether the bill in circulation is a damaged bill.

This invention also provides a method and system that are able to identify damaged bills for a variety of currencies.

The method and system of this invention illuminate the test bill using transmission light and reflection light and detect light transmitted through the test bill and light reflected from the test bill. The reflected and transmitted light intensities from the detected transmitted light and the detected reflected light are used to determine a disorder curve for the test bill.

A length of the disorder curve is compared with a length of a predetermined disorder curve for a reference bill. An evaluation factor is generated by comparing the lengths of the two disorder curves. The evaluation factor is placed on an evaluation map, which indicates the degree of deterioration or damage of the test bill.

The method and system of this invention can be used to determine the extent of deterioration for various types of test bills at a high speed.

The method and system of this invention are applicable to all types of paper currency.

The method and system of this invention can be used by implementing an existing imaging system, including existing illumination devices and light sensor devices, already present in existing bill handling machines. Therefore, developing a new imaging system for the system and method of this invention is not necessary, reducing costs associated with manufacturing and installing the method and/or system of this invention.

Because the method and system of this invention are unique and include a determination that is very simple, the damaged bill detecting method and system of this invention can be implemented rapidly.

These and other advantages of the system and method of this invention will be described in or be apparent from the following description of the preferred embodiment.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

Figure 1:
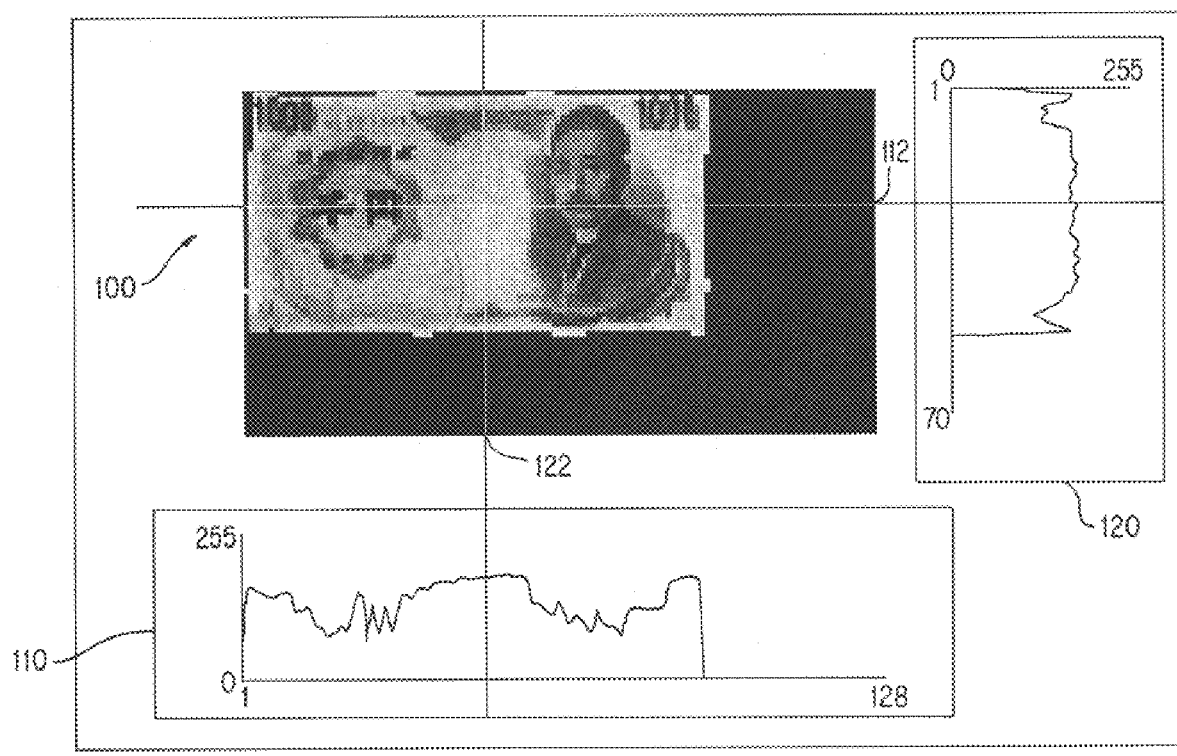
FIG. 1 shows a reflected light intensity image and exemplary reflected light intensity curves of a reference bill using a conventional method.
Figure 2:
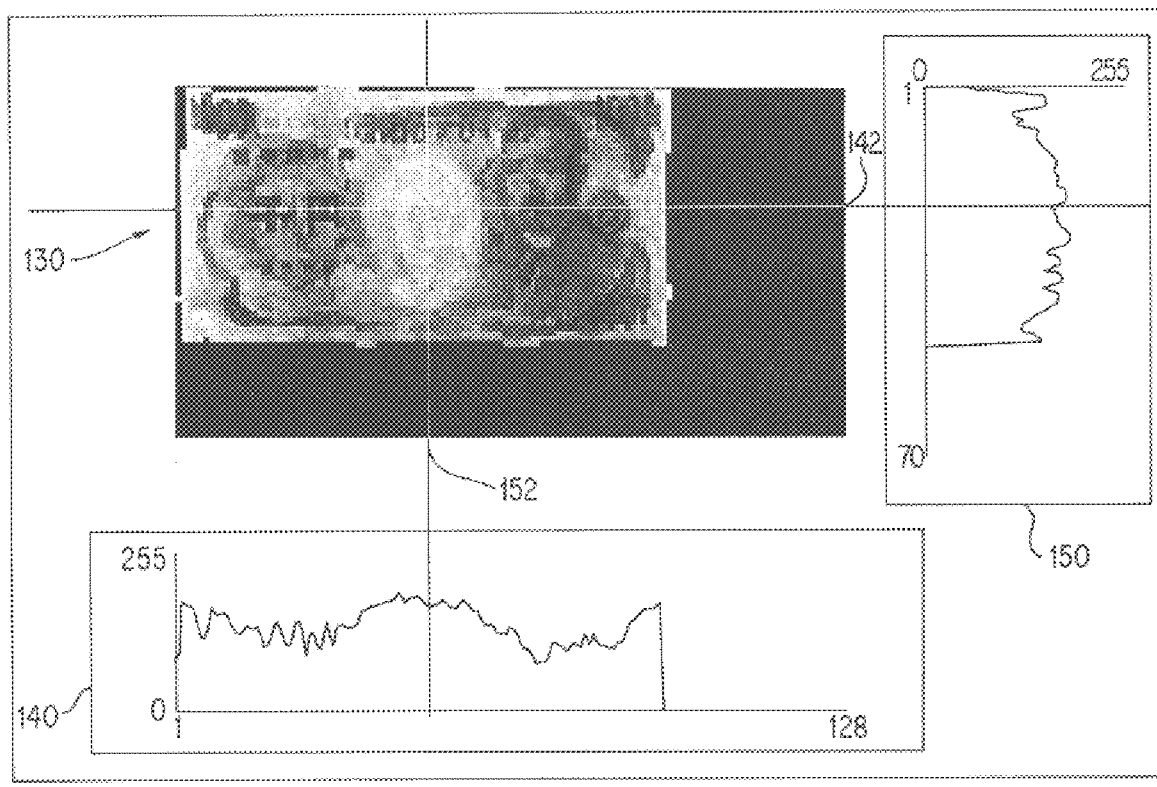
FIG. 2 shows a transmitted light intensity image and exemplary transmitted light intensity curves of the reference bill of FIG. 1 using the conventional method.

FIG. 1 depicts a reflected light intensity image 100 and corresponding exemplary reflected light intensity curves 110 and 120 for a reference bill obtained from an image sensor using the conventional non-contact optical method. The exemplary measured horizontal and vertical reflected light intensity curves 110 and 120 for the reference bill are the two curves adjacent to the reflected light intensity image 100. FIG. 2 depicts a transmitted light intensity image 130 and corresponding exemplary transmitted light intensity curves 140 and 150 for the reference bill in FIG. 1 obtained from an image sensor using the same conventional non-contact optical method. The exemplary measured horizontal and vertical transmitted light intensity curves 140 and 150 for the reference bill are the two curves adjacent to the transmitted light intensity image 130.

It should be appreciated that the exemplary reference horizontal reflected light intensity curve 110 and the exemplary reference vertical reflected light intensity curve 120 are the reference reflected light intensities for the reference reflected light intensity image 100 of the reference bill along the scan lines 112 and 122, respectively. Similarly, the exemplary reference horizontal transmitted light intensity curve 140 and the exemplary reference vertical transmitted light intensity curve 150 are the reference transmitted light intensities for the reference transmitted light intensity image 130 of the reference bill along the scan lines 142 and 152, respectively.

Figure 3:
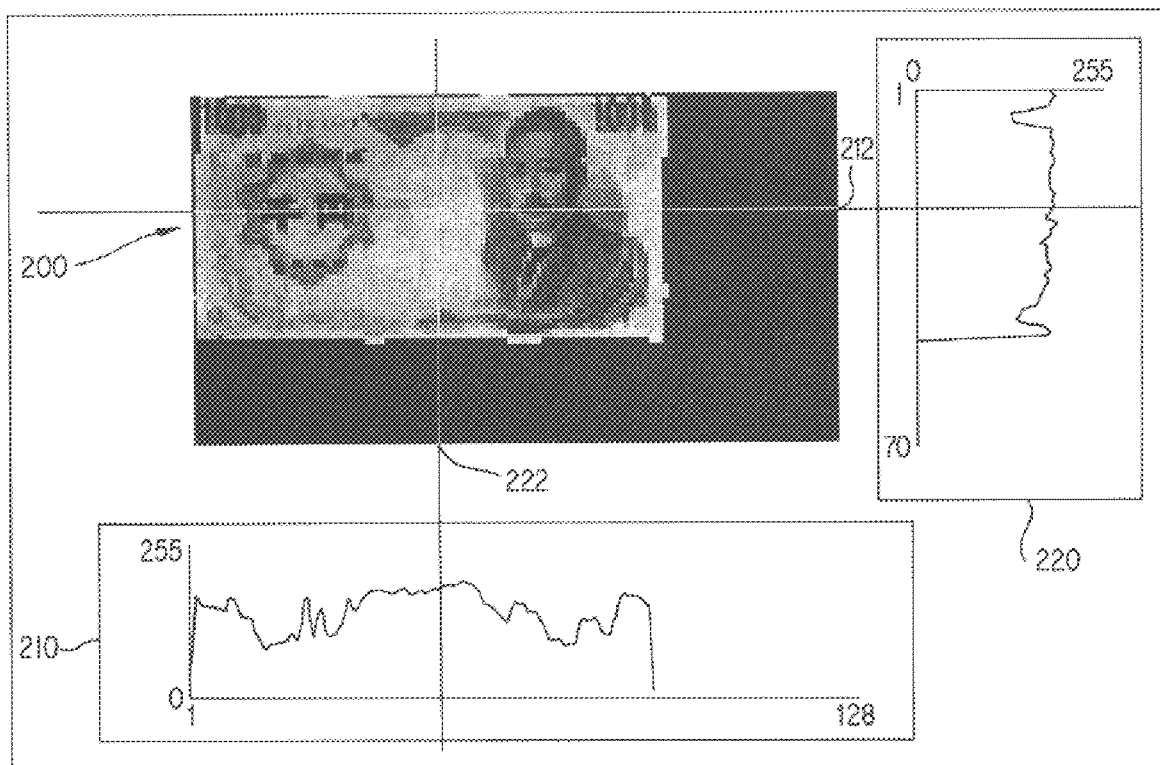
FIG. 3 shows a reflected light intensity image and exemplary reflected light intensity curves of a test bill using the conventional method.
Figure 4:
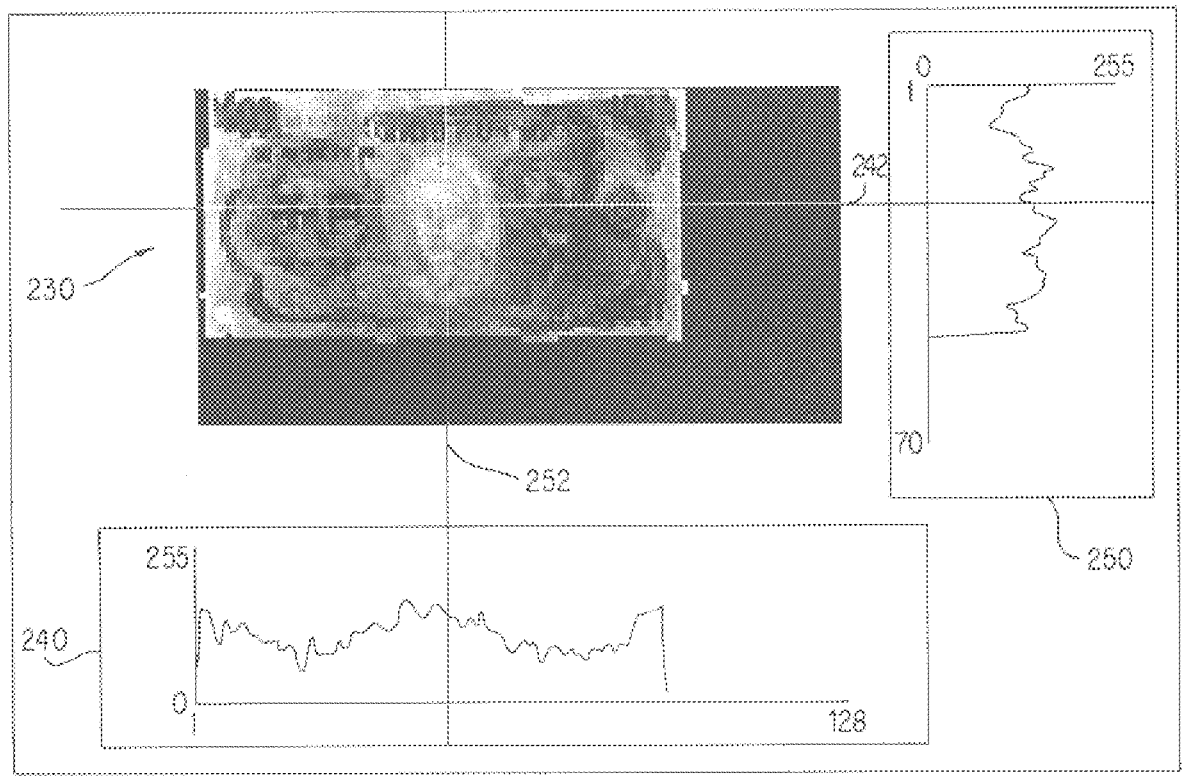
FIG. 4 shows a transmitted light intensity image and exemplary transmitted light intensity curves of the test bill of FIG. 3 using the conventional method.

FIG. 3 depicts a reflected light intensity image 200 and corresponding exemplary reflected light intensity curves 210 and 220 for a test bill obtained from an image sensor using the same conventional non-contact optical method used for the reference bill discussed above. The exemplary measured horizontal and vertical reflected light intensity curves 210 and 220 of the test bill are the two curves adjacent to the reflected light intensity image 200. FIG. 4 depicts a transmitted light intensity image 230 and corresponding exemplary transmitted light intensity curves 240 and 250 for the test bill in FIG. 3 obtained from an image sensor using the same conventional non-contact optical method. The exemplary measured horizontal and vertical transmitted light intensity 240 and 250 for the test bill are the two curves adjacent to the transmission image 230.

It should be appreciated that the exemplary measured horizontal reflected light intensity curve 210 and the exemplary measured vertical reflected light intensity curve 220 are the measured reflected light intensities for the measured reflected light intensity image 200 of the test bill along the scan lines 212 and 222, respectively. Similarly, the exemplary measured horizontal transmitted light intensity curve 240 and the exemplary measured vertical transmitted light intensity curve 250 are the measured transmitted light intensities for the measured transmitted light intensity image 230 of the test bill along the scan lines 242 and 252, respectively.

The conventional non-contact optical method then compares the reflected light intensity curve of the reference bill depicted in FIG. 1 to the reflected light intensity curve of the test bill depicted in FIG. 3, as well as the transmitted light intensity curve of the reference bill depicted in FIG. 2 to the transmitted light intensity curve of the test bill depicted in FIG. 4. A substantial difference between the reference bill and the test bill, corresponding to an evaluation factor derived from measured light intensity curves, is difficult to determine.

In contrast, the method and system according to this invention determine lengths of disorder curves for a reference bill and for a test bill and compare the determined lengths to generate an evaluation factor that represents the extent of deterioration of the test bill.

Preferably, the disorder curves are taken along one or more scan lines of the reflected and/or transmitted light intensity images. Preferably, the disorder curves are the horizontal and/or vertical light intensity curves of the reflected and/or transmitted light intensity images, although other disorder curves could be generated from other types of images of the reference and test bill could be used. Preferably, the length of the disorder curves are the Euclid lengths of the disorder curves, although any known method for determining a length of the disorder curves could be used. Preferably, the evaluation factor is a ratio of the lengths of the disorder curve for the reference bill and the disorder curve for the test bill. However, other methods for determining the evaluation factor could be used.

For a specified measurement unit, as the disorder curve becomes "smoother" or "rougher," the length of the disorder curve will be shorter or longer, respectively. In other words, as a bill becomes more damaged, the disorder curve will become either smoother and thus shorter, or rougher and thus longer, as compared to an undamaged reference bill. As such, as the length of the disorder curve for a damaged bill increases or decreases relative to the length of the disorder curve for the undamaged reference bill, the extent of damage to that bill correspondingly increases. Thus, the length of the disorder curve for a very faded or damaged bill is either much longer or much shorter than the length of the disorder curve for the undamaged reference bill.

Figure 5:
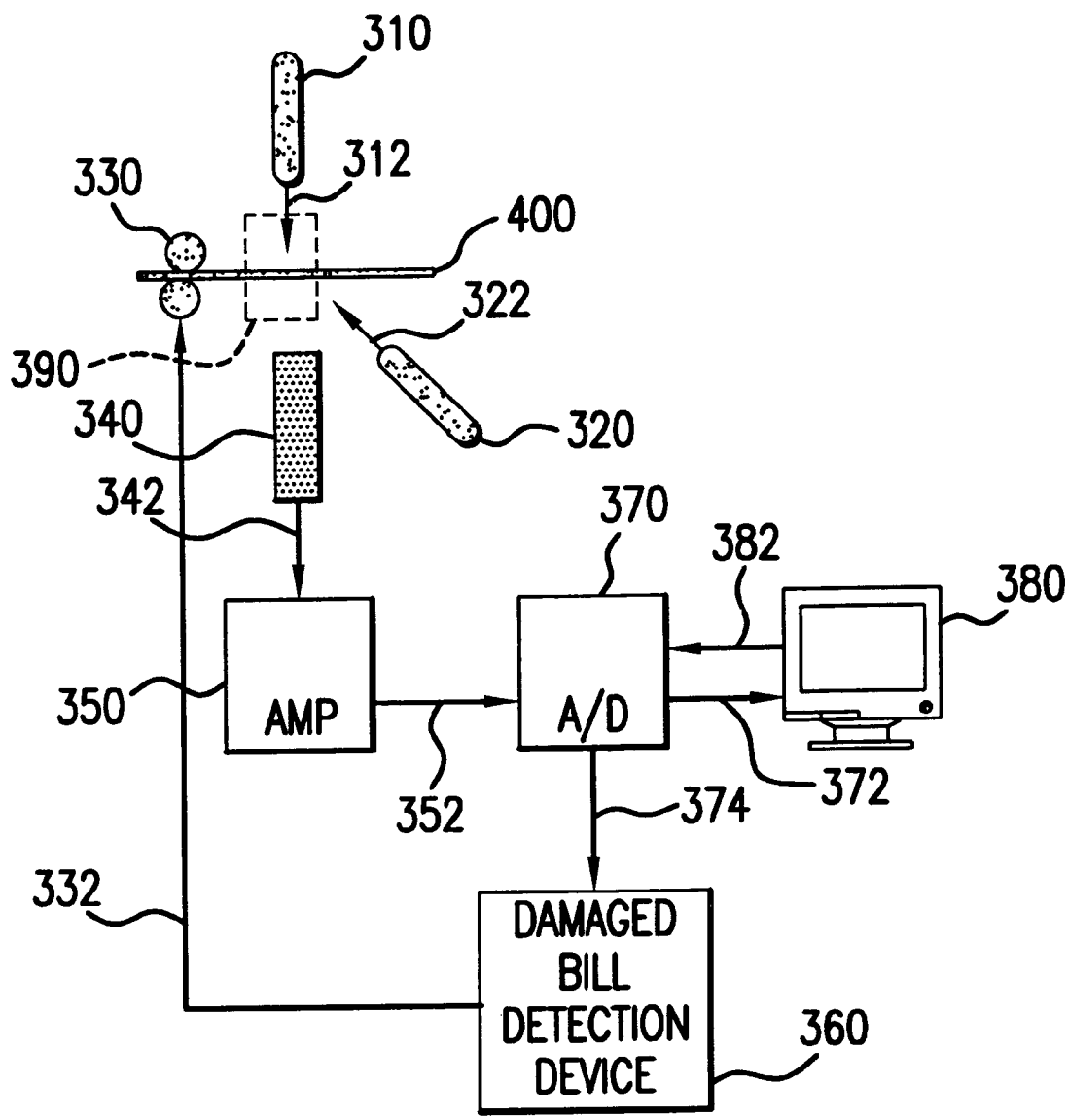
FIG. 5 is a schematic block diagram of a damaged bill detection system according to this invention.

FIG. 5 is a schematic and block diagram of a damaged bill detection system 300 according to this invention. The damaged bill detection system 300 includes a first light emitting device 310, a second light emitting device 320, a bill transport system 330, a light detecting device 340, an amplifier circuit 350, an analog-to-digital (A/D) converter 370, an optional display system 380, and a damaged bill detection device 360. It should be appreciated that the first and second light emitting devices 310 and 320 can be any known or later developed light emitting devices, such as a light emitting diode (LED) or a one-dimensional or two-dimensional array of such LEDs. It should also be appreciated that the bill transport system 330, which is represented by the pair of rollers shown in FIG. 5, can be any known or later developed bill transport system. Finally, it should be appreciated that the light detecting device 340 can be any known or later developed light detecting device, such as a photodiode, a one-dimensional or a two-dimensional array of photodiodes, a CCD, a one-dimensional or two-dimensional array of CCDs or the like. In particular, except as noted below, the particular structures and devices used to form the first and second light emitting devices 310, the bill transport system 330 and the light detecting device 340 are not critical to the operation of the method and system of this invention and thus any conventional devices or later developed devices can be equivalently used in the system and method of this invention without departing from its scope or spirit.

The amplifier 350, the damaged bill detection device 360 and the analog-to-digital converter 370 are preferably implemented using a programmed microprocessor or microcontroller and peripheral integrated circuit elements. However, it should be appreciated that these elements, and especially the damaged bill detector device 360, can be implemented on a programmed general purpose computer, a special purpose computer, an ASIC or other integrated circuit, a digital signal processor, a hard-wired electronic or logic circuit such as a discrete element circuit, a programmable logic device such as a PLD, PLA, FPGA or PAL, or the like. In general, any device, capable of implementing a finite state machine that is in turn capable of implementing the flow charts shown in FIGS. 9 and 10, can be used to implement the damaged bill detection device 360, and optionally the amplifier 350 and the analog-to-digital converter 370.

Furthermore, it should be appreciated that, while the damaged bill detection system 300 shown in FIG. 5 includes the display device 380, the display device 380 is not critical to the operation of the damaged bill detection system 300 according to this invention, and thus can be omitted without affecting the operation or performance of the damaged bill detection system 300. It should further be appreciated that, if the display device 380 is included, the display device 380 can be any known or later developed display device, such as a CRT, active or passive matrix LCD or active matrix LED display device. In general, any conventional or later developed display technology can be used to implement the display device 380.

In operation, the bill transport system 330 transports test bills through the damaged bill detection system 300 past the first and second light emitting devices 310 and 320. As each tested bill 400 is transported by the transport system 330, it is first illuminated by the first illumination device 310 using the light rays 312 which pass through the test bill 400 and are received by the light detection device 340 to generate a transmitted image of the bill 400. The test bill 400 is then illuminated by the second light emitting device 320 by the light rays 322 which are reflected off of the test bill 400 and received by the light detecting device 340 to form the reflected image.

Preferably, as each portion of the test bill 400 passes through an illumination zone 390, it is alternately illuminated by the first light emitting device 310 and then the second light emitting device 320. It should be appreciated that the dimensions of the illumination zone 390 correspond to the dimensions of the light detection elements in the light detecting device 340. Thus, if the light detection device 340 uses a one-dimensional array of light detecting elements, the illumination zone 390 will extend fully across the width of the test bill and the illumination zone along the direction of transport will extend a distance corresponding to the size of the detection elements in the one-dimensional detection array in the transport direction.

Preferably, as in conventional bill handling machines, the first light emitting device 310, which is used to form the transmitted image, emits light at both a first wavelength of approximately 570 $\mu$m and a second wavelength of approximately 940 $\mu$m, while the second light emitting device, which is used to generate the reflected image, also emits light at the first wavelength of approximately 570 $\mu$m and at the second wavelength of approximately 940 $\mu$m. It should be appreciated that it is not necessary that both, or even either, of the first and second light emitting devices 310 and 320 emit exactly two wavelengths of light. Thus, the first and second light emitting devices 310 and 320 can each emit one, two, or more wavelengths of light, so long as the emitted wavelengths are detectable by the light detection device 340.

The amount of the transmitted light 312 passing through the test bill 400 is detected by the light detection device 340 and is output as one or more transmitted light intensity signals over the signal line 342 to the amplifier 350. Similarly, the light 322 reflected from the test bill 400 is detected by the light detection device 340 and is output as one or more reflected light intensity signals over the signal line 342 to the amplifier 350. It should be appreciated that the intensity of the light 312 transmitted through the test bill 400 is affected by many factors. These factors include the amount of dirt and/or ink on the bill, the distribution of the ink on the bill, the design of the bill, and the fatigue of the bill. Similarly, the intensity of the light 322 reflected from the bill 400 is also affected by numerous factors. These factors include wrinkles caused by folding the bill and the wear and tear the bill has been subjected to. Because the factors affecting the intensity of the transmitted light are generally independent of the factors affecting the intensity of the reflected light, the test bill 400 should be tested using both the transmitted light 312 and the reflected light 322. In general, the light detecting element or elements of the light detector 340 outputs analog signals.

The amplified analog light intensity signals are then output by the amplifier 350 over a signal line 352 to the analog-to-digital converter 370. The analog-to-digital converter converts the amplified analog values of the reflected light intensity signals and the transmitted light intensity signals to digital values. The analog-to-digital converter 370 outputs these signals over a signal line 372 to the display device 380, if it is provided, and over a signal line 374 to the damaged bill detection device 360. The damaged bill detection device 360 compiles the digital reflected and transmitted light intensity signals into reflected and transmitted light intensity images, respectively.

Figure 6:
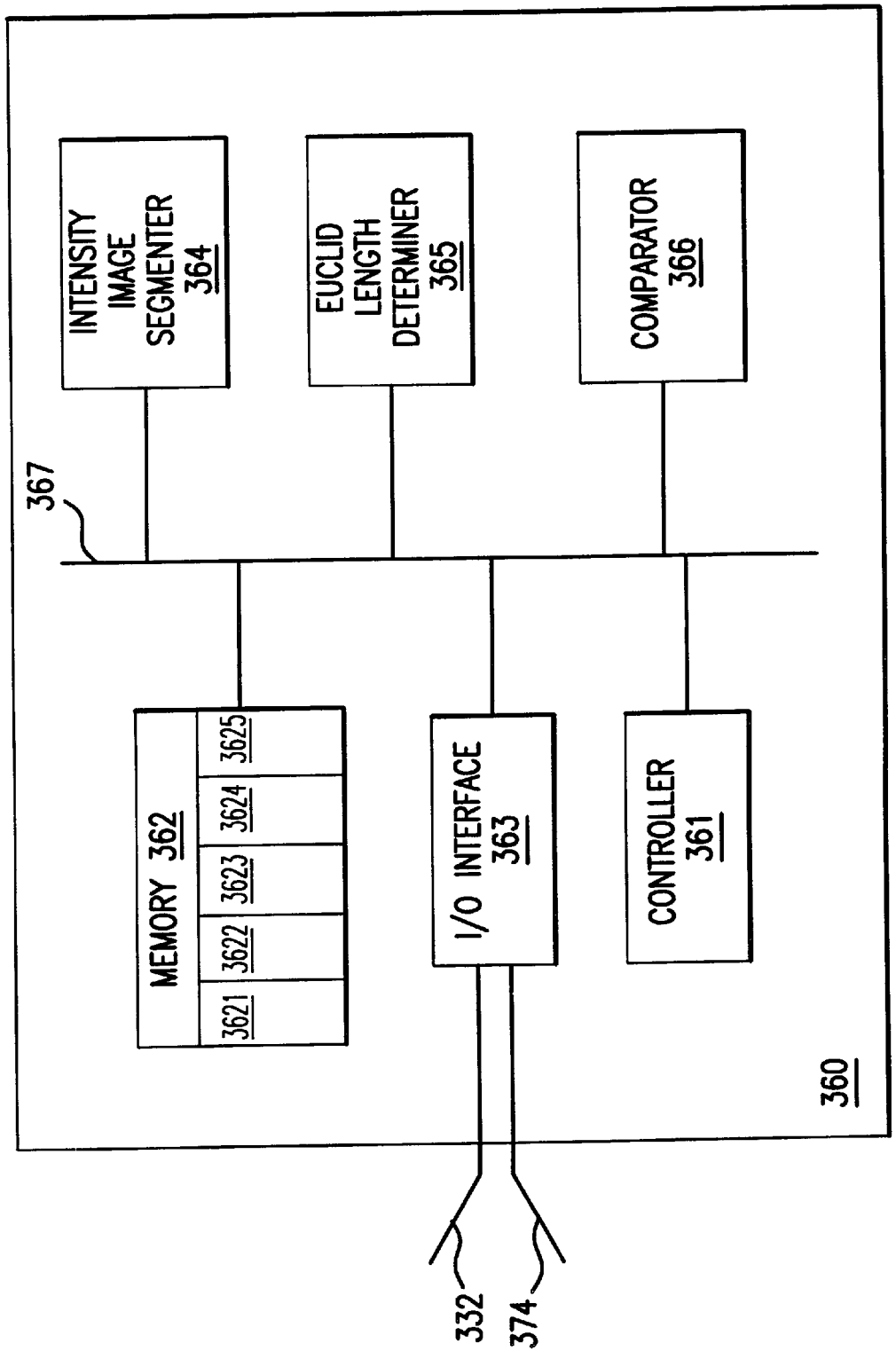
FIG. 6 is a block diagram showing the damaged bill detection device in greater detail.

FIG. 6 shows the damaged bill detection device 360 in greater detail. As shown in FIG. 6, the damaged bill detection device 360 includes a controller 361, a memory 362, an input/output (I/O) interface 363, an intensity image segmenter 364, a disorder curve length determiner 365, a comparator 366 and a data/control bus 367. The input/output interface 363 is connected to the signal line 374 from the analog-to-digital converter 370 and to a signal line 332, which provides control signals to the transport system 330.

The memory 362 includes a reference disorder curve length portion 3621 that stores reference disorder curve lengths for reference bills for each block for each of the different wavelengths output by the light emitting devices 310 and 320 and corresponding to whether the light intensity image is a reflected or transmitted light intensity image. The memory 362 also includes an intensity data portion 3622 which stores the reflected and transmitted light intensity images. The memory 362 also includes a determined disorder curve length portion 3623 which stores the determined disorder curve lengths determined by the disorder curve length determiner 365 for each of the blocks of the current light intensity image generated by the intensity image segmenter 364. The memory 362 further includes an evaluation factor portion 3624 which stores the evaluation factors generated for each of the determined disorder curve lengths for each of the blocks of the current intensity image. Finally, the memory 362 includes an evaluation criterion factor portion 3625 which stores the evaluation criterion factors $\gamma_o$ for each of the reflected and transmitted light intensity images and for each of the different degrees of damage into which the test bill 400 can be classified.

Figure 9:
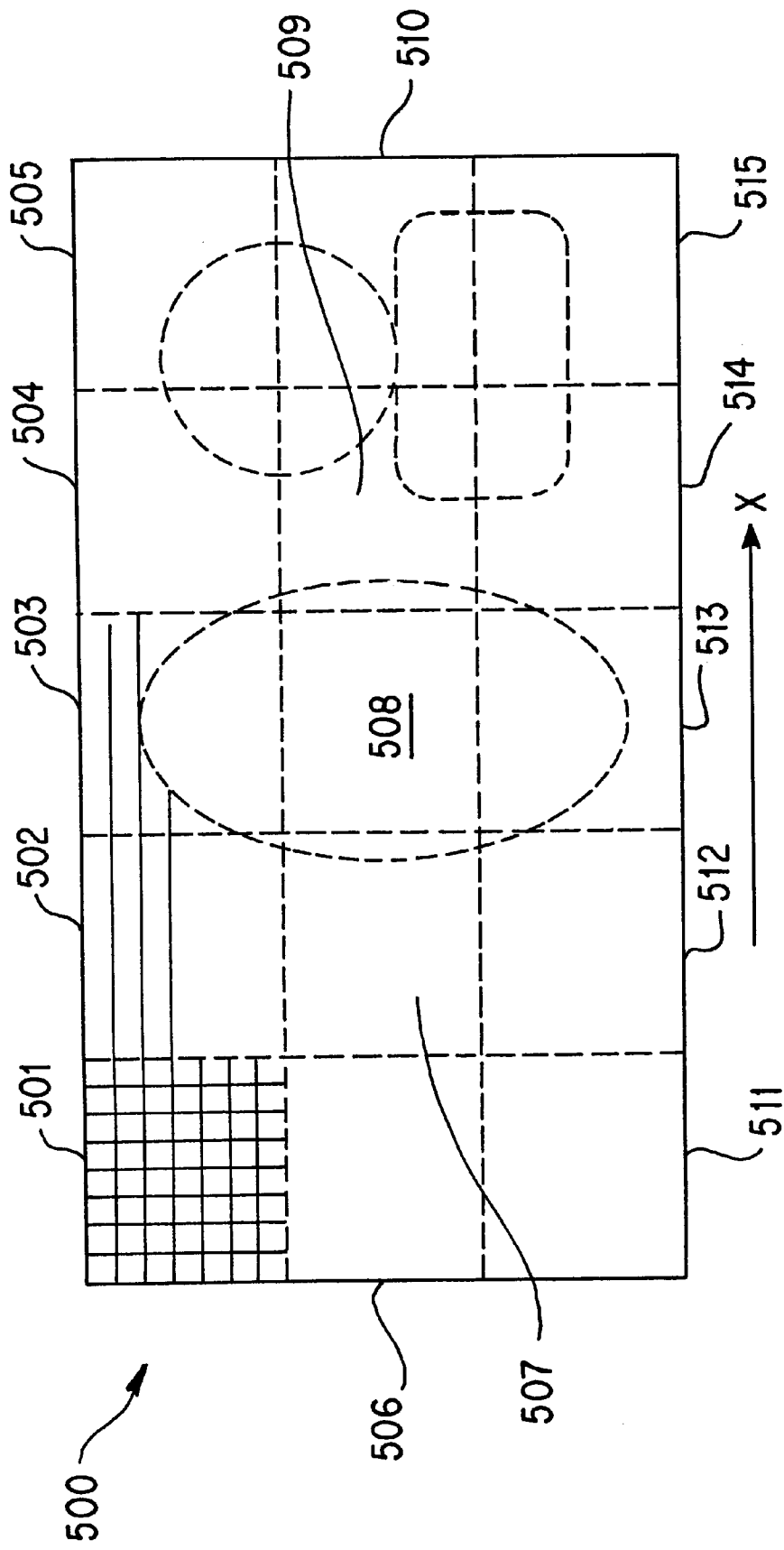
FIG. 9 illustrates how a test bill's reflected or transmitted light intensity image is divided into numerous regions.

In operation, the input/output interface 363 receives the digitized transmitted and reflected light intensity signals at the one or more different wavelengths, and, under control of the controller 360, stores the digitized reflected and transmitted light intensity signals in the intensity data portion 3622 of the memory 362 to form the reflected and transmitted light intensity images. Then, the intensity data for a particular wavelength and a particular transmitted or reflected light intensity image is output from the intensity data portion 3622 to the intensity image segmenter 364 as a current intensity image. The intensity image segmenter 364 divides the intensity data for the current intensity image into a plurality of blocks corresponding to different portions of the test bill 400, as shown in FIG. 9 and discussed in detail below. The intensity image segmenter 364 then outputs each of the blocks of the current intensity image to the disorder curve length determiner 365.

The disorder curve length determiner 365 then determines one or more disorder curve lengths for the current block of the current intensity image being analyzed. The disorder curve length determiner 365 then outputs the determined lengths of the one or more disorder curves for each of the blocks of the current intensity image to the determined disorder curve length portion 3623 of the memory 362 under control of the controller 361.

It should be appreciated that the lengths of the disorder curves could be determined along any orientation. Preferably, in the system and method according to this invention, the lengths of the disorder curves are determined along both the horizontal and vertical orientations of the test and reference bills. Thus, for each different test image, and for each block into which the light intensity images of the test bill are divided, a corresponding horizontal disorder curve length and a corresponding vertical disorder curve length are determined. Moreover, the reference disorder curve length portion 3621 of the memory 362 preferably stores the corresponding horizontal reference disorder curve length and the corresponding vertical reference disorder curve length for each block of each of the different light intensity images of the test bill.

Once all of the lengths of the one or more disorder curves for each of the blocks of the current intensity image are determined, under control of the controller 361, the lengths of the disorder curves for each block and the reference bill's corresponding disorder curve lengths for that block are output from the determined disorder curve length portion 3623 and the reference disorder curve length portion 3621 to the comparator 366.

Because the system and method according to this invention preferably use horizontal and vertical disorder curves, the comparator 366 generates a horizontal evaluation factor $\gamma_x$ and a vertical evaluation factor $\gamma_y$ for the current block. These evaluation factors for each block are then stored in the evaluation factor portion 3624 of the memory 362. Once all of the horizontal and vertical disorder curve lengths for all of the blocks of all of the generated light intensity images have been compared to the corresponding reference disorder curve lengths by the comparator 366, and the resultant evaluation factors have been stored in the evaluation factor portion 3624, the controller 361 determines at least one maximum evaluation factor $\gamma_{max}$ and/or one minimum evaluation factor $\gamma_{min}$ from among the various horizontal evaluation factors $\gamma_x$ and the various vertical evaluation factors $\gamma_y$ for the test bill. Preferably, the at least one maximum evaluation factor $\gamma_{max}$ and/or one minimum evaluation factor $\gamma_{min}$ includes at least one maximum transmitted light evaluation factor $\gamma_{maxt}$ and/or one minimum transmitted light evaluation factor $\gamma_{mint}$ from among the various horizontal evaluation factors $\gamma_x$ and the various vertical evaluation factors $\gamma_y$ for the one or more transmitted light intensity images. Similarly, the at least one maximum evaluation factor $\gamma_{max}$ and/or one minimum evaluation factor $\gamma_{min}$ preferably includes at least one maximum reflected light evaluation factor $\gamma_{maxr}$ and/or one minimum reflected light evaluation factor $\gamma_{minr}$ from among the various horizontal evaluation factors $\gamma_x$ and the various vertical evaluation factors $\gamma_y$ for the one or more reflected light intensity images.

It should be appreciated that various factors affect how damage to the test bill affects the length of the determined disorder curves. For example, depending on one or more of the type of media, the type of ink or the like used to form the test bill and the reference bill, the disorder curve determined along the horizontal orientation of the test bill could be shorter or longer than the disorder curve determined along the horizontal orientation of the reference bill. Similarly, the disorder curve determined along the vertical orientation of the test bill could be shorter or longer than the disorder curve determined along the vertical orientation of the reference bill. Furthermore, the horizontal disorder curve for the test bill could be shorter than the horizontal disorder curve for the reference bill, while the vertical disorder curve for the test bill is longer than the vertical disorder curve for the reference bill, or vice-versa.

Figure 18:
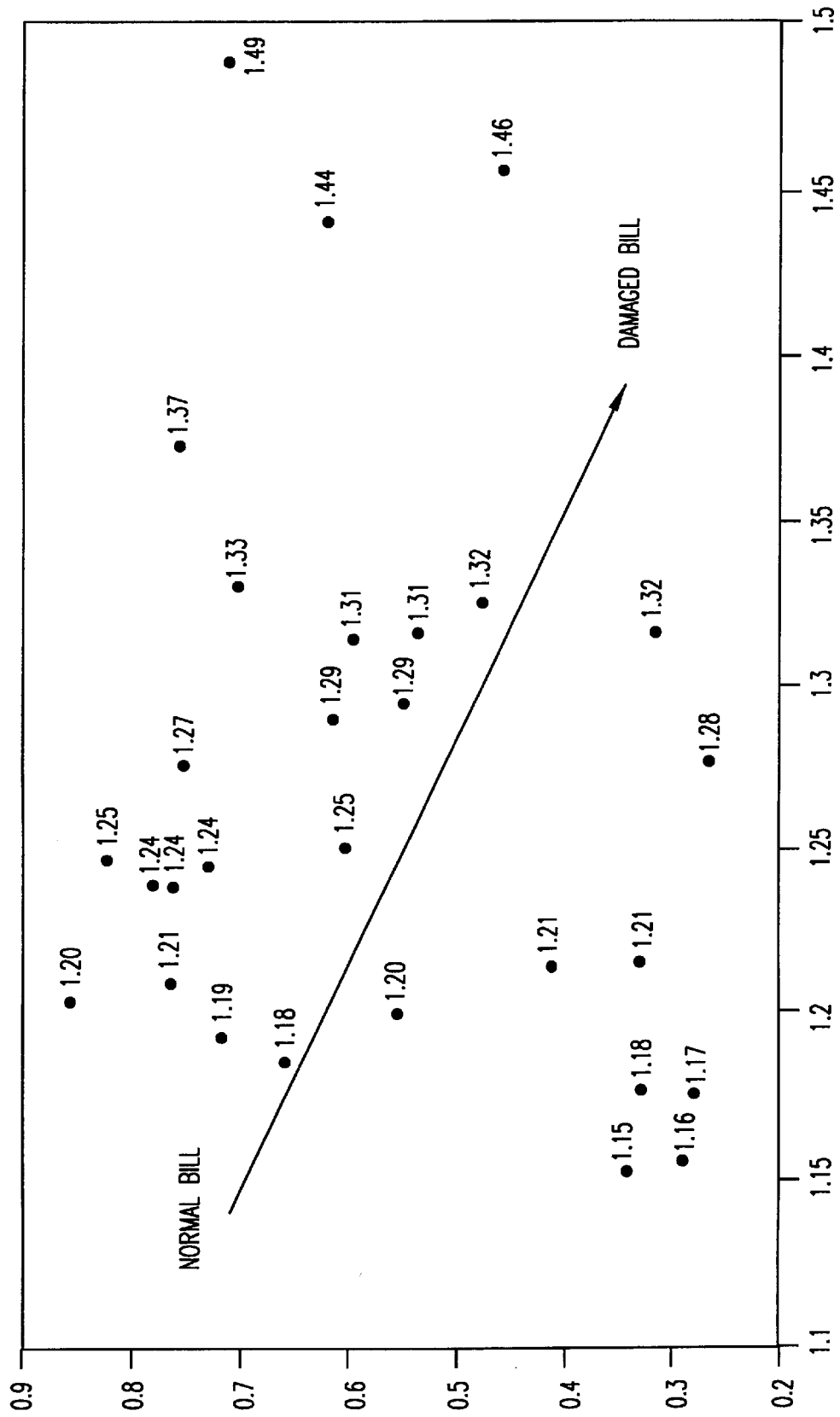
FIG. 18 is an evaluation map similar to FIG. 17, where U.S. dollar bills were used as the test bills.

It should also be appreciated that the disorder curve lengths for each of the different types of sensed light output by the light emitting devices can vary depending on the type of bill being tested. For example, the disorder curve length of a reflected light intensity image for one type of test bill can be longer than the disorder curve length of that type of reference bill, while the disorder curve length of a transmitted light intensity image of that type of test bill can be shorter than the disorder curve length of that type of reference bill, or vice-versa. This situation is shown in FIG. 18.

For another type of bill, the disorder curves for both the reflected and transmitted light intensity images are both longer, or both shorter, than the corresponding disorder curves for the reference bill under similar circumstances.

In other words, because the disorder curves determined for each type of bill can be dependent upon the type of bill measured, and/or the type of measurement, the evaluation factors are dependent on the type of bill to be measured. Thus, the controller 361 determines at least one maximum evaluation factor and/or one minimum evaluation factor to more accurately represent the difference in the length of the disorder curve for the reference bill and the test bill.

The comparator 366 then compares the maximum evaluation factor $\gamma_{max}$ and/or minimum evaluation factor $\gamma_{min}$ with one or more evaluation criteria factors $\gamma_o$. Based on the comparison with these evaluation criteria factors, the controller 361 determines whether the test bill is a damaged bill and the extent of the damages or deterioration to the test bill.

It should be appreciated that the comparison is repeated for each of the different light intensity images that could be generated based on the different wavelengths of light generated by the light emitting devices 310 and 320 and the different reflected and/or transmitted light intensity signals that can be generated for each of those wavelengths. Thus, it should be appreciated that the particular reference disorder curve lengths selected from the reference disorder curve length portion 3621 of the memory 362 will depend upon the particular wavelength of light used to generate the intensity signal being tested and whether that intensity signal is a reflected light intensity signal or a transmitted light intensity signal.

It should also be appreciated that the ultimate determination as to whether the test bill is a damaged bill does not need to be delayed until all of the testing for all of the different light intensity signals has been completed, although it should be so delayed to maximize the probability that the damaged bill determination correctly determines whether the test bill is damaged or not. That is, as each of the evaluation factors $\gamma_x$ and $\gamma_y$ for each block of each of the different reflected and transmitted light intensity images are generated, these factors can be compared against a threshold, which, if exceeded, assures that the test bill will be determined to be a damaged bill requiring special processing or handling by the bill handling machine. In such a case, as soon as the appropriate threshold is exceeded, there is no need to continue processing, because, even if the threshold were exceeded by a higher value, that would not change the ultimate determination that the test bill is a damaged bill requiring special handling.

Thus, based upon the at least one maximum evaluation factor $\gamma_{max}$ and/or one minimum evaluation factor $\gamma_{min}$ for the different wavelengths and transmitted and reflected light intensity images, and the corresponding evaluation criterion factors $\gamma_o$, the controller 361 determines whether the test bill 400 is a damaged bill or not and outputs the resultant signal on the signal line 332 to the transport system 330. If the test bill 400 is not a damaged bill, the control signal output on the signal line 332 causes the transport system 330 to transport the test bill 400 further into the bill handling machine for further processing. Otherwise, if the test bill 400 is a damaged bill, the control signal output on the signal line 332 cause the transport system 330 to return the test bill 400 back along the transport path to the input/output slot of the bill handling machine to return the bill, if the bill handling machine is part of a vending machine or the like, or to transport the damaged test bill 400 to a damaged bill repository for special handling, such as to remove the damaged bill from circulation.

Figure 7:
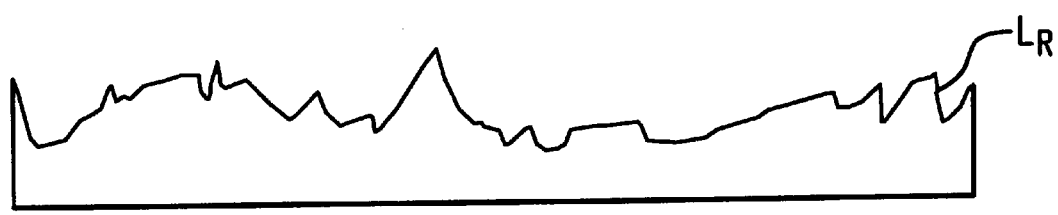
FIG. 7 is an exemplary disorder curve of an exemplary reference bill.
Figure 8:
FIG. 8 is an exemplary disorder curve of an exemplary test bill.

FIG. 7 illustrates a disorder curve of a reference bill. FIG. 8 illustrates a disorder curve of a test bill. In FIG. 7, $L_R$ represents the length of the disorder curve for the reference bill for a particular type of light intensity image, reflected or transmitted, at a particular wavelength. Similarly, in FIG. 8, $L_D$ represents the length of the disorder curve for the test bill for the particular type of light intensity image, reflected or transmitted, at the particular wavelength. Because the test bill will always have more damage or deterioration than the reference bill, the length $L_D$ of the test bill will always be different than the length $L_R$ of the reference bill.

The evaluation factor $\gamma$ expresses the ratio of the length of the disorder curves for a particular type of light intensity signal of a particular wavelength:

$$\gamma = L_D / L_R$$

It should be noted that it is within contemplation of this invention to express the difference in the length of the corresponding disorder curves in other ways, such as, for example, a difference between the lengths:

$$\gamma = |L_D - L_R|$$

Thus, it should be appreciated that different evaluation factors $\gamma$ will be generated for each of the reflected and transmitted light intensity images and for each different wavelength for which each reflected and transmitted light intensity images has been generated.

It should also be appreciated that a maximum evaluation factor $\gamma_{max}$ and/or a minimum evaluation factor $\gamma_{min}$ is used, whichever is more representative of the difference between the disorder curve length of the test bill and the disorder curve length of the reference bill, to determine the extent of damage or deterioration of the test bill. As such, a maximum evaluation factor or a minimum evaluation factor may be derived from the use of a ratio to determine the evaluation factor, whereas only a maximum evaluation factor will be derived when an absolute value relationship is measured.

The evaluation factors $\gamma$ are used to distinguish damaged test bills from acceptable test bills based on the comparison between the $L_D$ values for the test bill and the $L_R$ values for the reference bill. Thus, even if the conventional statistical parameters generated by directly comparing the intensity signal profiles, such as those shown in FIGS. 1–4, of the test and reference bills are very similar, the evaluation factors $\gamma$ can be used to identify the extent of any deterioration of the test bill because any disorder curve length $L_D$ of the test bill should always be different than the corresponding disorder curve length $L_R$ of the reference bill.

As shown in FIG. 9, the image 500 for each light intensity image, reflected and transmitted, for each light wavelength obtained from the test bill 400 is divided or segmented into multiple blocks, segments or regions 501 et seq. The image 500 is divided into these regions 501 et seq. because the test bill 400 may suffer damage only in one or more specific portion or area. For example, as shown in FIG. 9, the images 500 of the test bill 400 are preferably divided into fifteen (15) regions 501–515. However, the image 500 can each be divided into any number of regions or blocks. In fact, increasing the number of regions increases the accuracy in detecting the extent of deterioration of the test bill.

Thus, as shown in FIG. 9, the corner blocks 501, 505, 511 and 515 are very likely to have high disorder curve lengths curve resulting from bent and/or torn corners. Similarly, the blocks 503, 508 and 513 are very likely to have large disorder curve lengths due to folds resulting when the test bill 400 is folded in half. In contrast, the blocks 502, 504, 506, 507, 509, 510, 512 and 514 are not as likely to be damaged. If the entire image 500 for the test bill 400 were treated as a single block and the disorder curve lengths were determined for the entire image 500, the high damage areas, such as the blocks 501, 503, 505, 508, 511, 513 and 515, would be averaged with the low damage blocks 502, 504, 506, 507, 509, 510, 512 and 514. Thus, if a bill were highly damaged but only in one of the blocks 501–515, the difference for the disorder curve lengths for the entire image 500 relative to the disorder curve lengths for an entire reference image would be much less significant than the difference in the disorder curve lengths for a highly damaged block 501–515 and the disorder curve lengths of the corresponding block of the reference image. Thus, by dividing the image 500 into a plurality of blocks 501–515, a damaged bill which is damaged only in one, or in a few specific ones, of the blocks 501–515 can be more easily detected.

Figure 10:
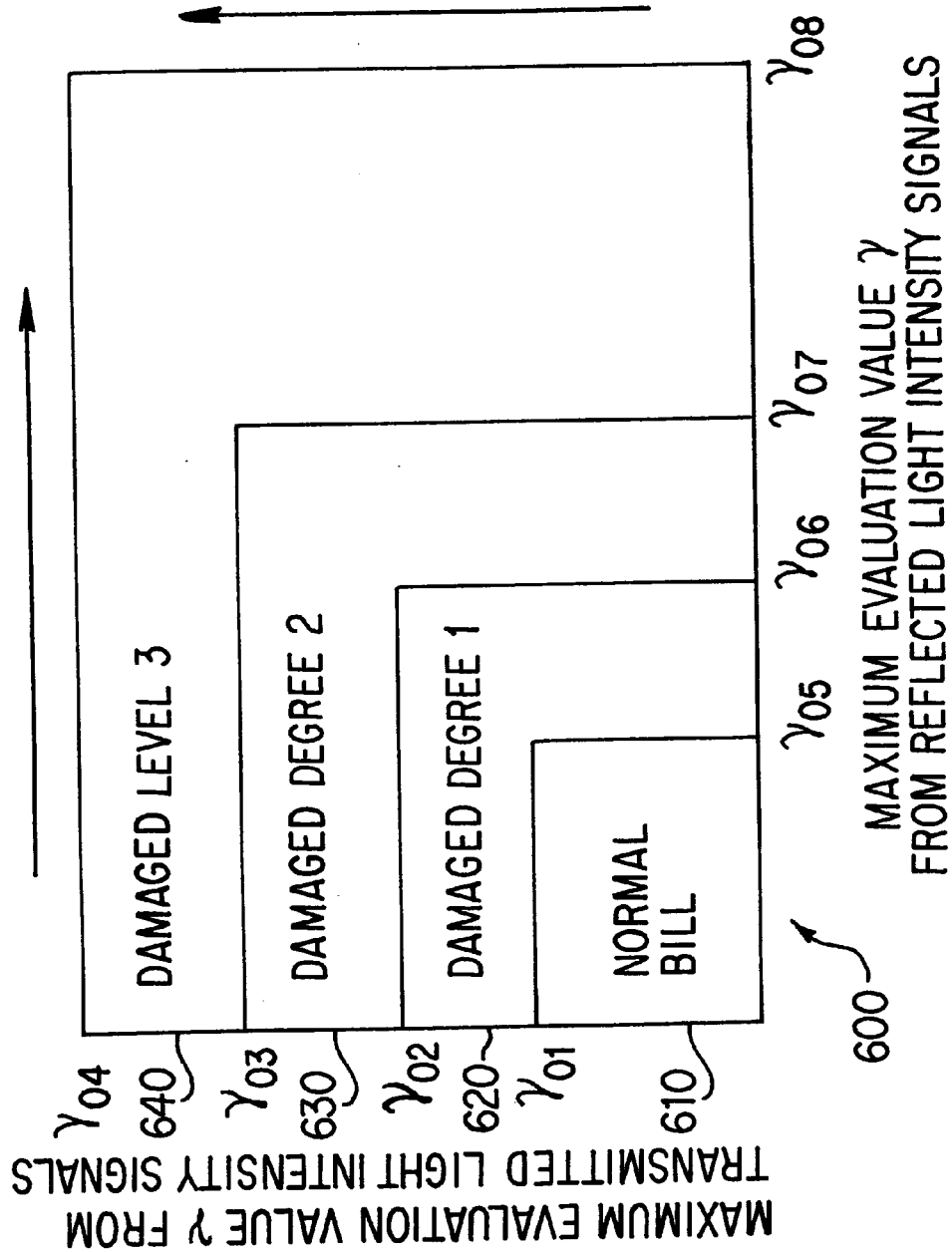
FIG. 10 is an evaluation map for determining the extent of damage to a test bill.

FIG. 10 shows an evaluation map 600 for determining the extent of damage to a test bill 400, where increasing damage to the test bill results in increased disorder curve lengths, and thus increased maximum evaluation factors for both transmitted and reflected light intensity images. As shown in FIG. 10, the evaluation map 600 is separated into a number of damage level zones 610–640 indicative of the extent of the damage to the test bill. For example, the damage level zone 610 indicates an acceptable amount of damage that will normally occur to any bill in circulation, but which does not represent sufficient damage to warrant labeling the test bill a "damaged" bill. The damage level zones 620–640 indicate a worsening of the damage to the test bill. Thus, as shown in FIG. 10, if the maximum evaluation factor $\gamma_{maxt}$ for the transmitted light intensity images is less than the reference evaluation factor for the reference transmitted light intensity image $\gamma_{01}$ and, at the same time, the maximum evaluation factor of $\gamma_{maxr}$ for the reflected light intensity images is less than the reference factor $\gamma_{05}$ for the reference reflected light intensity image, the test bill 400 is determined to be a normal bill. If, as shown in FIG. 18, increased damage to the test bill results in shorter disorder curve lengths for one or both of the transmitted or reflected light intensity images, the minimum evaluation factor $\gamma_{min}$, if determined as a ratio, would be used to determine if the test bill were a normal bill.

Figure 11:
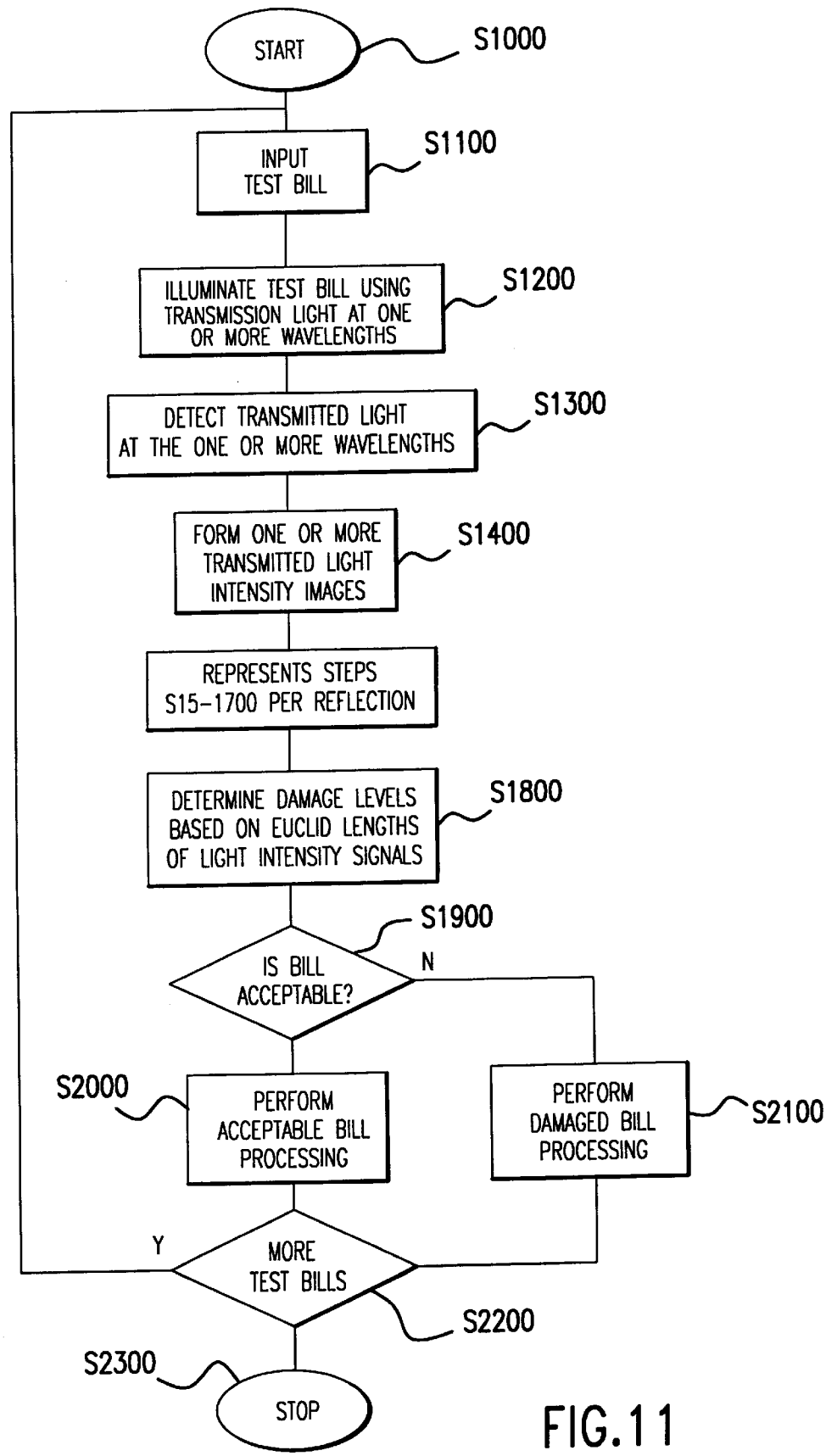
FIG. 11 is a flowchart outlining a method for detecting damaged bills according to this invention.

FIG. 11 is a flowchart outlining one embodiment of the method for determining whether a bill is damaged according to this invention. Beginning in step S1000, control continues to step S1100, where a test bill is input. Then, in step S1200, the test bill is illuminated using transmission light at one or more wavelengths. Next, in step S1300, the transmitted light transmitted through the test bill is detected. Then, in step S1400, one or more transmitted light intensity images corresponding to the one or more transmitted light wavelengths are formed from the detected transmitted light. Control then continues to step S1500.

In step S1500, the test bill is illuminated using reflection light at one or more wavelengths. Then, in step S1600, the reflected light at the one or more wavelengths is detected. Next, in step S1700, one or more reflected light intensity images are formed from the detected reflected light at the one or more wavelengths. Control then continues to step S1800.

In step S1800, damage levels for each of the one or more transmitted light intensity images and the one or more reflected light intensity images are determined based on the one or more disorder curve lengths for each of the transmitted and reflected light intensity images. Then, in step S1900, the input test bill is determined to be acceptable or not based on the determined damage levels. If the test bill is acceptable, control continues to step S2000. Otherwise, if the test bill is not acceptable, control jumps to step S2100.

In step S2000, any further acceptable bill processing is performed on the acceptable test bill. Control then jumps to step S2200. In contrast, in step S2100, any further damage bill processing is performed on the damaged test bill. Control then continues to step S2200.

In step S2200, the system determines if there are any further bills to be tested. If so, control jumps back to step S1100. Otherwise control continues to step S2300, where the damaged bill determining process according to this invention stops.

Figure 12:
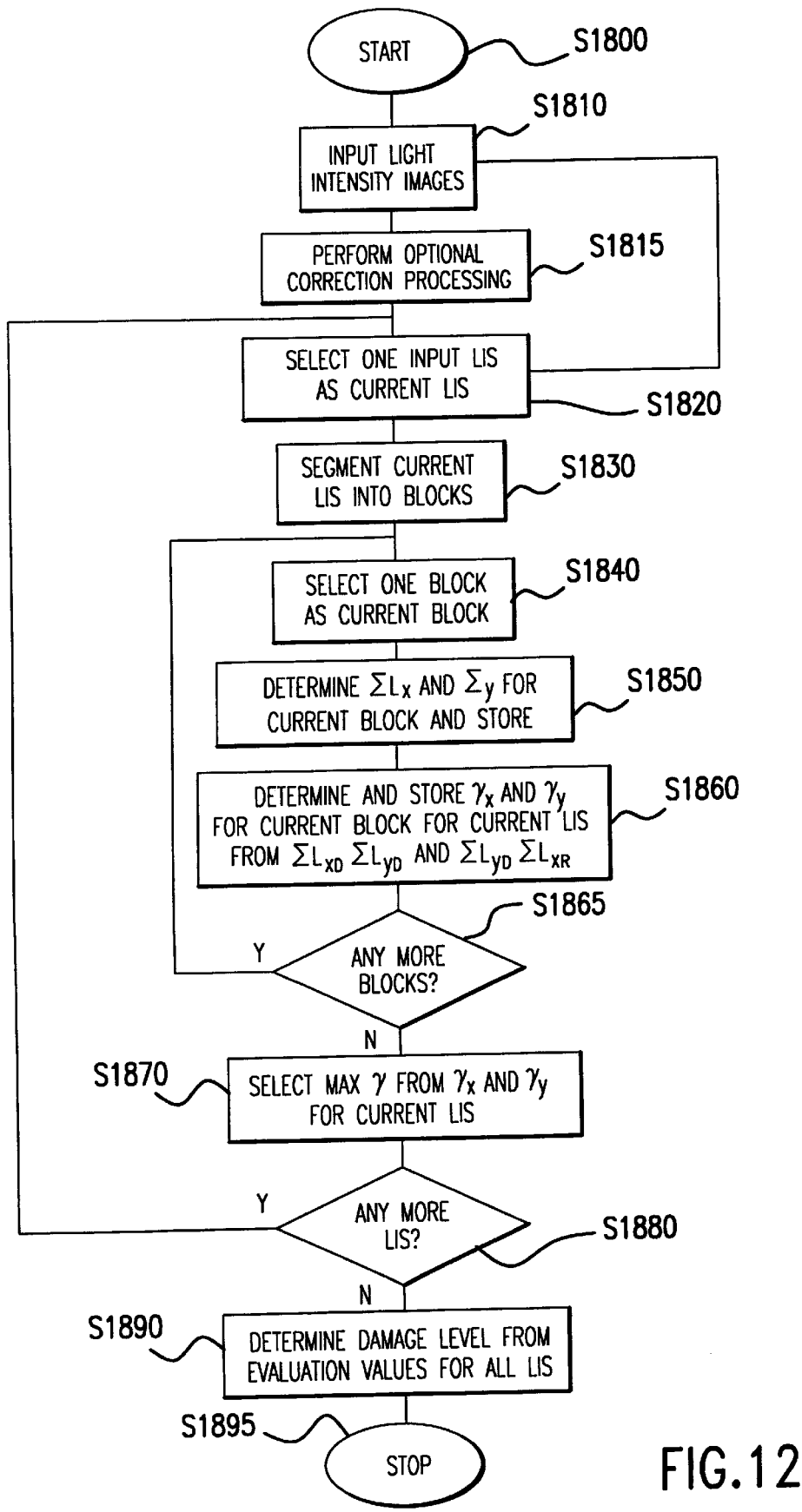
FIG. 12 is a flowchart outlining in greater detail the process for determining whether the test bill is a damaged bill according to this invention.

FIG. 12 shows the damage level determining process of step S1800 in greater detail. Beginning in step S1800, control continues to step S1810, where the one or more reflected light intensity images and the one or more transmitted light intensity images are input. Control then optionally continues to step S1815, or optionally jumps to step S1820. In step S1815, any necessary or desirable correction processing is performed before the light intensity images are analyzed. This optional correction processing can include correcting for image inclination or filtering the images to delete any noise or other distortions generated in detecting the transmitted and reflected light in steps S1300 and S1600. If step S1815 is performed, control then continues to step S1820.

In step S1820, one of the input light intensity images is selected as the current light intensity image. Then, in step S1830, the current light intensity image is segmented into a plurality of blocks. Next, in step S1840, one of the blocks of the current light intensity image is selected as a current block. Control then continues to step S1850.

In step S1850, the horizontal disorder curve length $\Sigma L_x$ and the vertical disorder curve length $\Sigma L_y$ for the current block are determined. Then, in step S1860, the evaluation factors $\gamma_x$ and $\gamma_y$ for the current block of the current light intensity image are determined based on the determined horizontal and vertical disorder curve lengths $\Sigma L_x$ and $\Sigma L_y$ for the current block of the current light intensity image and the corresponding reference horizontal and vertical disorder curve lengths $\Sigma L_{xr}$ and $L_{yr}$ for the current block of the reference image corresponding to the current light intensity image, and the evaluation factors are then stored. Control then continues to step S1865.

It should be appreciated, as set forth above, that, in step S1860, the evaluation factors $\gamma_x$ and $\gamma_y$ are determined as the ratio of the horizontal disorder curve lengths for the current block for the current light intensity image and the current block for the reference image corresponding to the current light intensity image. Alternately, as set forth above, the evaluation factors $\gamma_x$ and $\gamma_y$ could be determined by any other mathematical function of the disorder curve lengths for the current block of the current light intensity image and the current block of the reference image corresponding to the current light intensity image, such as the absolute value of the difference. Once the evaluation factors $\gamma_x$ and $\gamma_y$ are determined, these factors are stored.

Then, in step S1865, the control routine determines whether any more blocks of the current light intensity image need to be analyzed. If so, control returns to step S1840, where a next one of the blocks of the current light intensity image is selected as the current block. Otherwise, if no more blocks of the current light intensity image need to be analyzed, control continues to step S1870. In step S1870, the largest evaluation factor from all of the horizontal and vertical evaluation factors $\gamma_x$ and $\gamma_y$ for the current light intensity image is selected as the maximum evaluation factor $\gamma_{max}$ for the current light intensity image. Control then continues to step S1880.

In step S1880, the control routine determines whether there are any more light intensity images which need to be segmented and analyzed. If so, control jumps back to step S1820, where a next one of the input light intensity images is selected as a current light intensity image. Otherwise, control continues to step S1890.

In step S1890, the damage level zone for the input test bill is determined based on the maximum evaluation factors $\gamma_{max}$ for the one or more transmitted light intensity images and for the one or more reflected light intensity images, based on the evaluation map shown in FIG. 10 corresponding to the particular input test bill. If, as shown in FIG. 18, increased damage to the test bill results in shorter disorder curve lengths for one or both of the transmitted or reflected light intensity images, one or more minimum evaluation factor $\gamma_{min}$, if determined as a ratio, would be used in step S1870 instead of the maximum evaluation factor $\gamma_{max}$, and the one or more minimum evaluation factor $\gamma_{min}$ would be used in step S1890 to determine the degree of damage of the test bill compared to a normal bill. Control then continues to step S1895, where control returns to step S1900.

To test the method and system according to this invention, thirty (30) U.S. one-dollar bills and forty (40) Japanese 1000-yen bills were analyzed. The bills used to test the method and system according to this invention were subjected to different types of damage commonly occurring to currency in circulation. Also, each bill was tested a number of times to the evaluate the repeatability of the method and system according to this invention.

Figure 13:
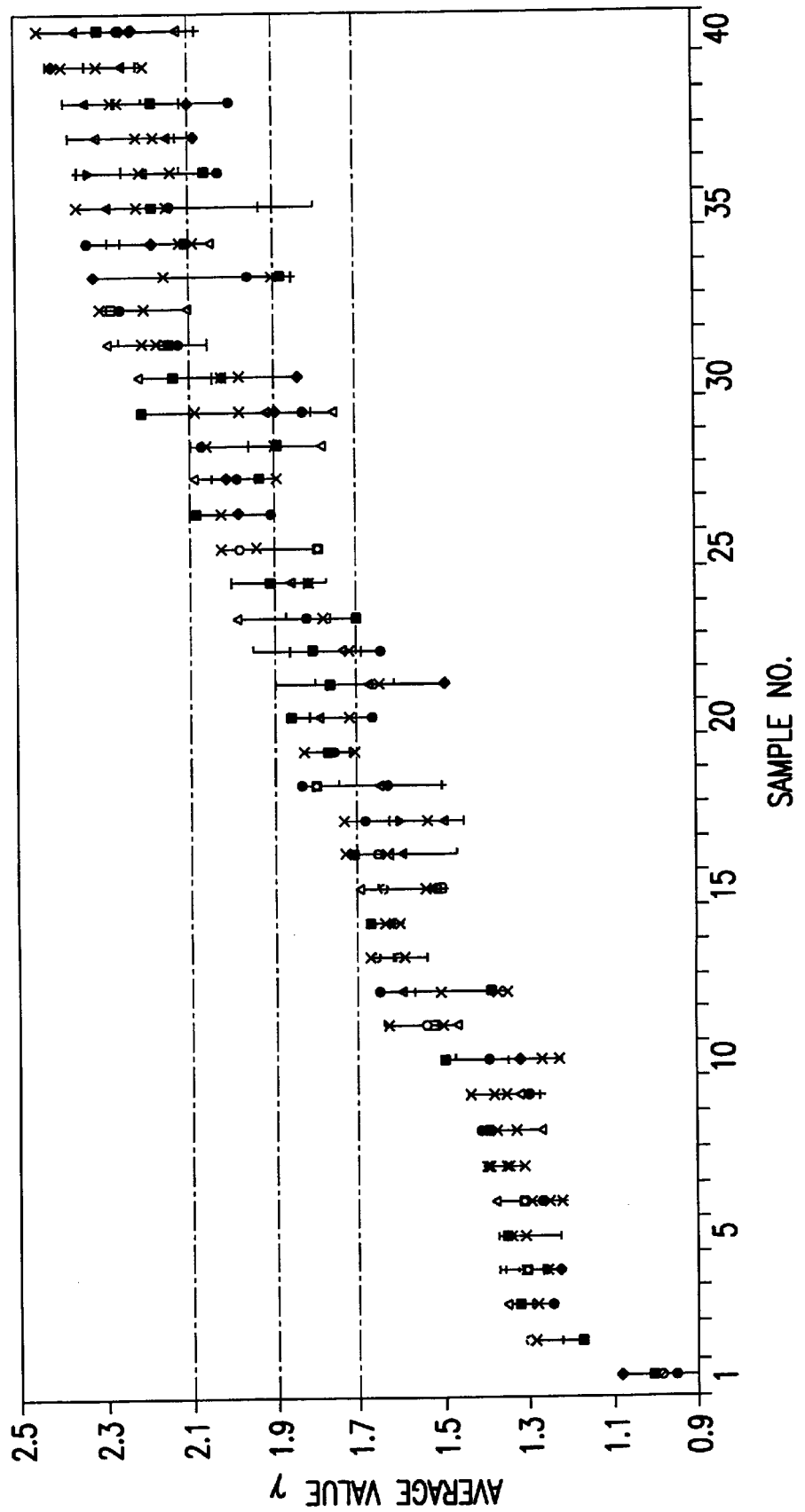
FIG. 13 is a graph illustrating the range of results obtained from the transmitted light intensity images of Japanese test bill samples generated using an infrared light source having an emitted light wavelength of approximately 970 μm.
Figure 14:
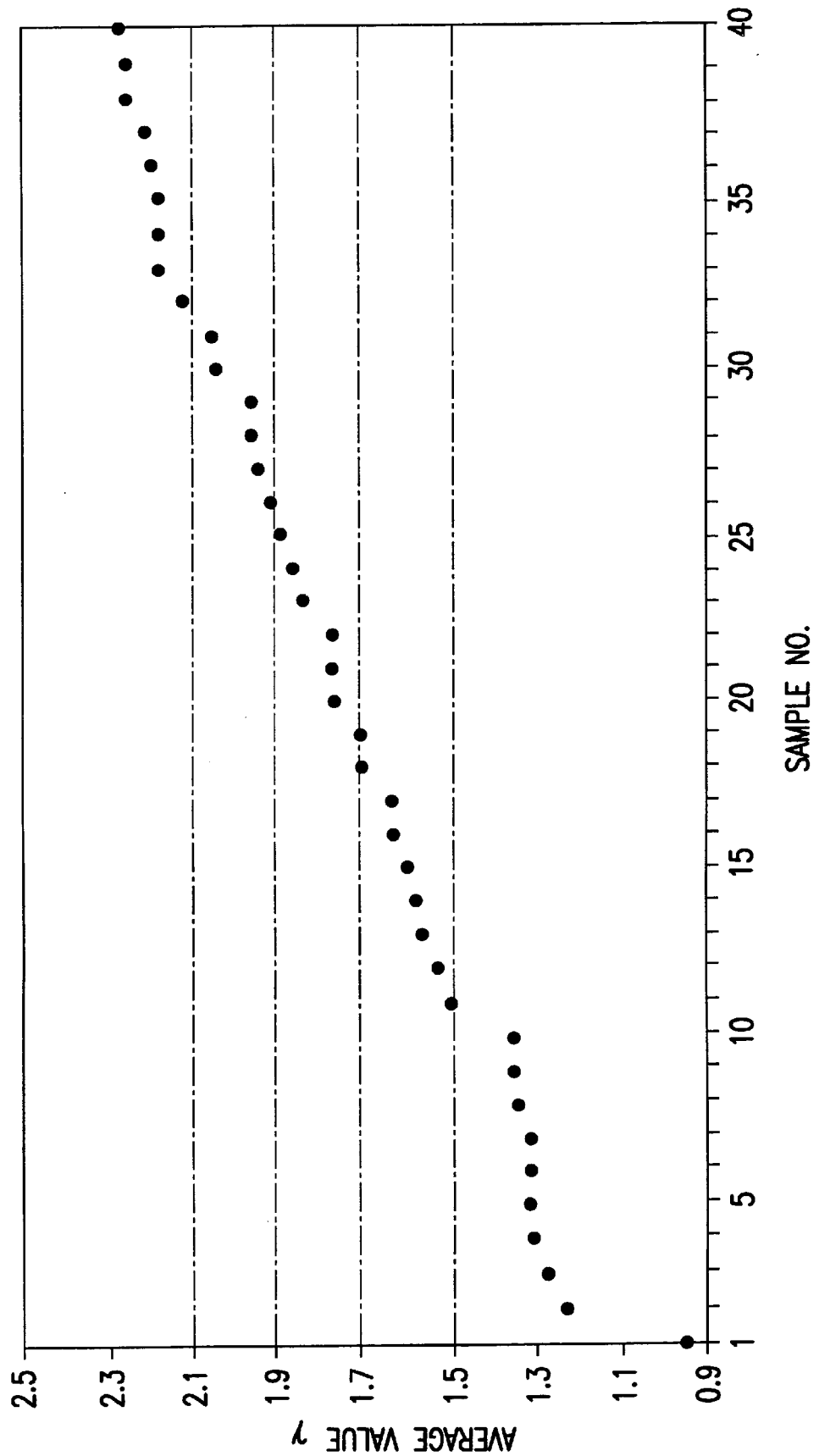
FIG. 14 is a graph illustrating the average value of eight tests of each sample in FIG. 13.

FIG. 13 graphically shows the ranges of evaluation factors $\gamma$ obtained for the number of tests based on transmitted light images generated using the 40 1000-yen samples. The 1000-yen samples were exposed to infrared emitted light having a wavelength of approximately 970 $\mu$m. Specifically, each sample was tested eight times, although no significance should be given to the specific number of tests. FIG. 14 graphically shows an average $\gamma$ factor of each of the 40 1000-yen samples.

In FIGS. 13 and 14, the test samples are ordered from sample 1 to sample 40 along the horizontal axis, and are ordered according to the extent of damage to each sample. Thus, sample 1 represents the sample 1000-yen bill with the least amount of detected damage, while sample 40 represents the most-damaged 1000-yen bill. The vertical axis indicates the evaluation factor $\gamma$ value for each sample. The experimental results shown in FIGS. 13 and 14 demonstrate that the resulting evaluation factors indicate the extent of deterioration to each bill.

Figure 15:
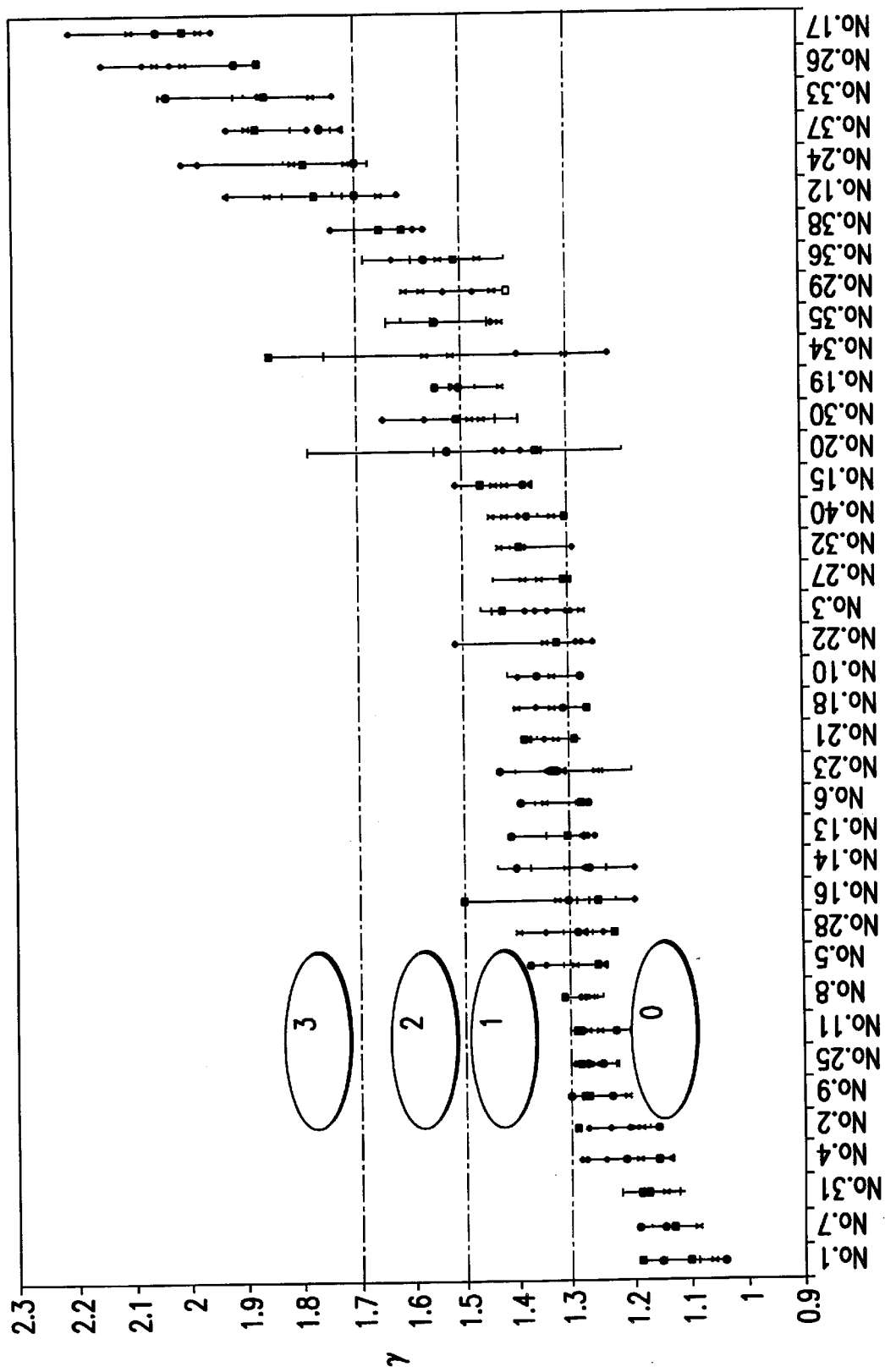
FIG. 15 is a graph illustrating the range of results obtained from the reflected light intensity images of Japanese test bill samples generated using the infrared light source having the emitted light wavelength of approximately 970 μm.
Figure 16:
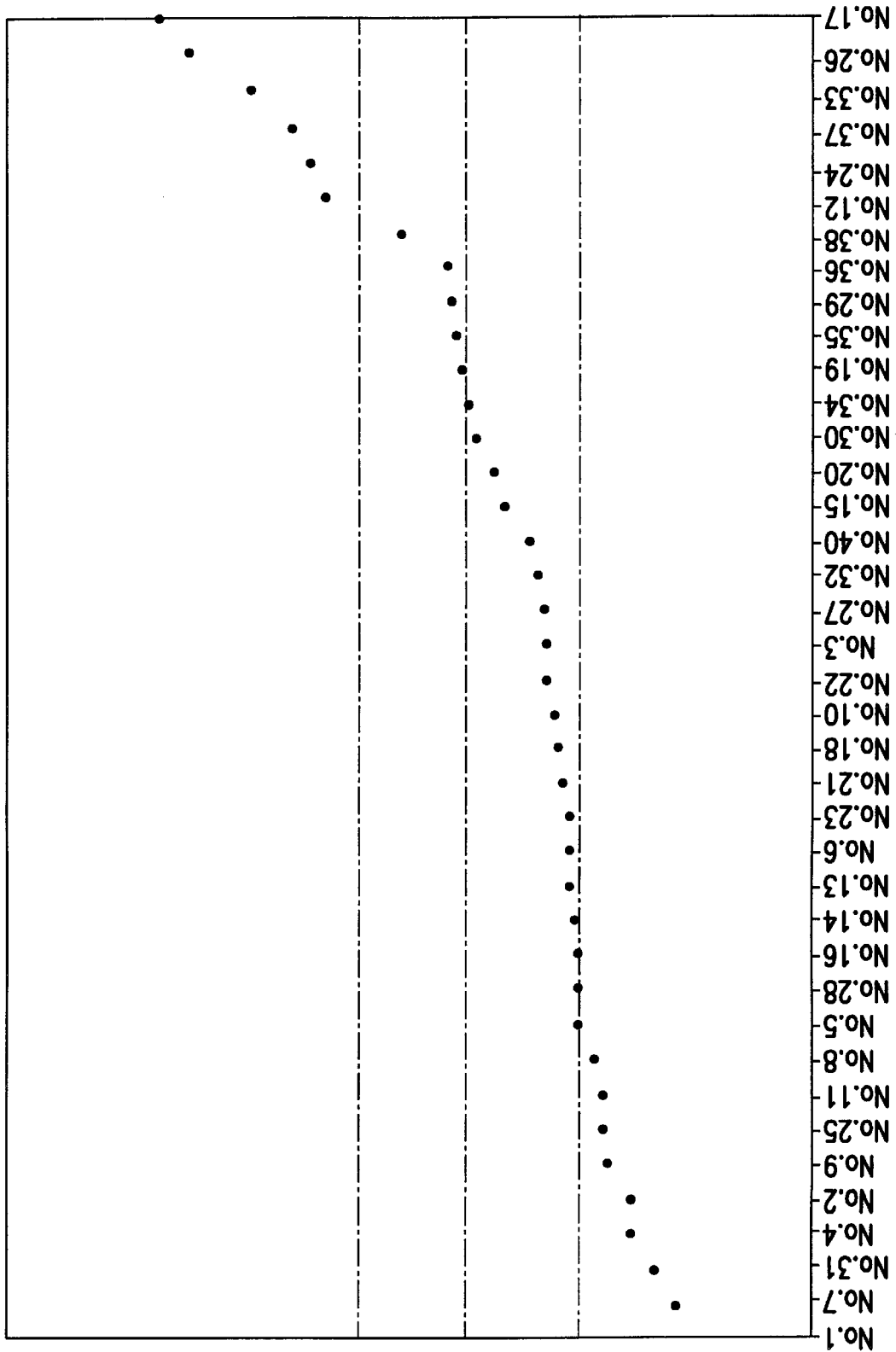
FIG. 16 is a graph illustrating the average value of eight tests of each sample in FIG. 15.

FIG. 15 graphically shows the range of evaluation factors $\gamma$ obtained for the number of tests based on reflected light images generated using the same 40 1000-yen samples. The samples were exposed to infrared emitted light having a wavelength of approximately 970 $\mu$m. The results represent the values for each bill, again tested eight times. FIG. 16 graphically shows the average evaluation factor $\gamma$ value for each of the 40 1000-yen samples.

The reflected light intensity image values are related mainly to the condition of the bill surface, such as wrinkles, surface texture and the like. The test samples are ordered along the horizontal axis of FIG. 16 according to each bill's surface condition, which does not correspond to the damage amount used to order the samples in FIGS. 13 and 14. Thus, in FIGS. 15 and 16, the samples are shown out of sample order. According to the test results, sample 1 is determined to be the most normal or least damaged bill, while sample 17 is determined to be the most damaged bill. As such, the generated evaluation factor $\gamma$ is associated with the surface condition of each bill.

Figure 17:
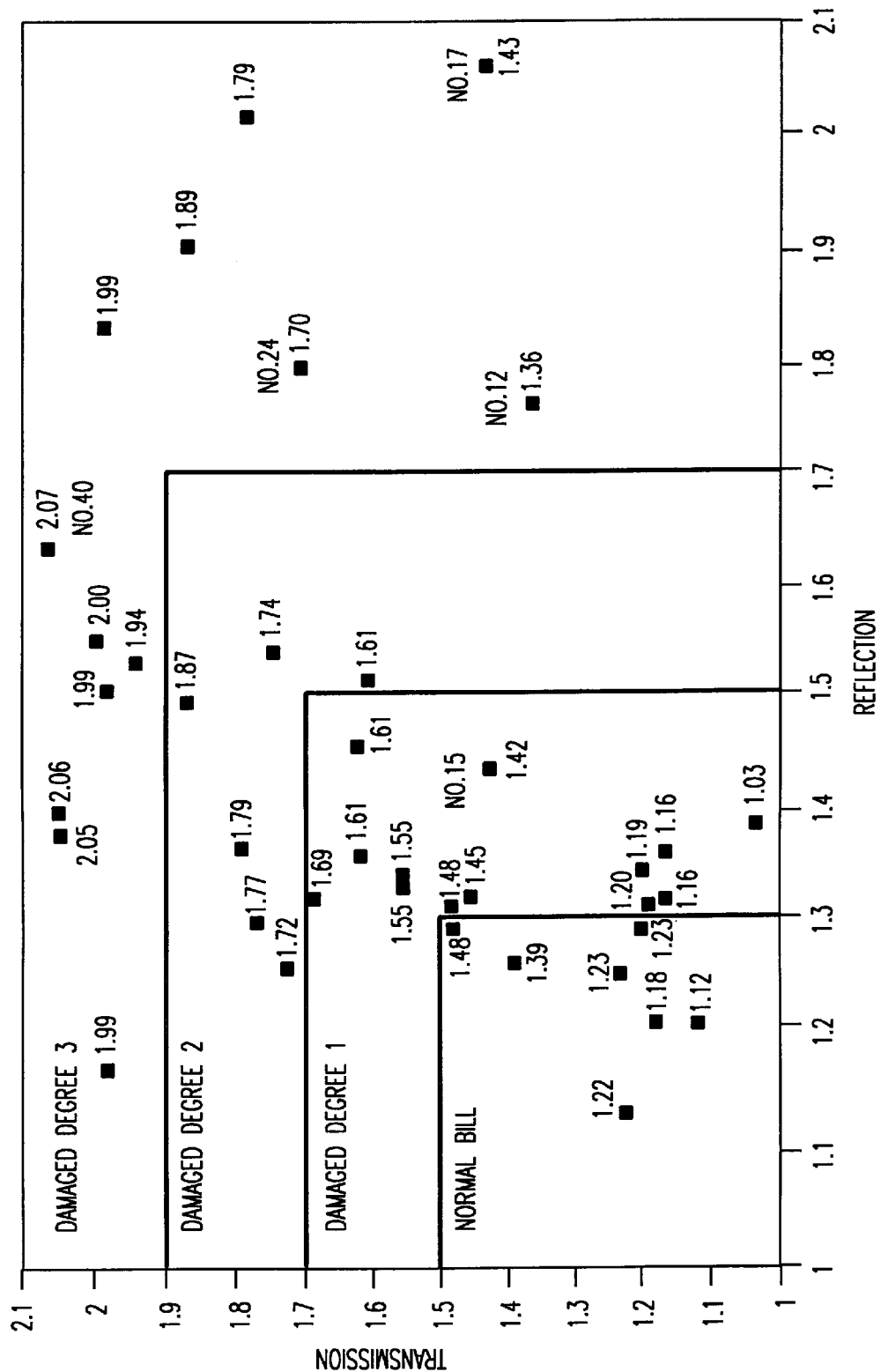
FIG. 17 is an evaluation map used to interpret the results shown in FIGS. 14 and 16.

FIG. 17 shows the evaluation map for 1000-yen bills, along with the evaluation factors $\gamma$ shown in FIGS. 14 and 16. The horizontal axis represents the evaluation factor values derived from reflected light intensity images of the 40 1000-yen samples. The vertical axis represents the evaluation factor values derived from transmitted light images of the 40 1000-yen samples.

Thus, by looking at the evaluation map shown in FIG. 17, the extent or degree of deterioration of each of the 40 1000-yen samples is determined by the position of each bill's reflected light and transmitted light evaluation factor values on the evaluation map. For example, sample 2 has a transmitted light evaluation factor value of 1.12, and a reflected light evaluation factor value of 1.22 which places it in the normal or acceptable bill region. Bill No. 29 has an evaluation factor value of 1.74 and a reflected light evaluation factor value of 1.53, which places it in the damaged degree 2 region. Depending on an acceptable damage degree level, a determination would have to be made as to whether bill No. 29 should be defined as a "damaged" bill, and thus rejected by a bill-handling machine or removed from circulation.

FIG. 18 shows the evaluation map for the 30 dollar samples discussed above. As shown in FIG. 18, the horizontal axis represents the reflected light evaluation factors $\gamma$ determined from the reflected light intensity images, while the vertical axis represents the transmitted light evaluation factor values $\gamma$ determined from the transmitted light intensity images. Similarly to Yen bills, for dollar bills for reflected light evaluation factors $\gamma$, increasing values for $\gamma$ indicates increasing damage to the bills. However, in contrast to Yen bills, for dollar bills, decreasing values for $\gamma$ indicates increasing damage to the bills in the case of transmitted light evaluation factors $\gamma$. Thus, by looking at the evaluation map shown in FIG. 18, the extent or degree of the deterioration of each of the 30 dollar samples is determined by the position of each bill's reflected light and transmitted light evaluation factors $\gamma$ on the evaluation map.

While this invention has been described in conjunction with the specific embodiments of this invention, it is evident that many alternatives, modifications and variations may be apparent to these skilled in the art. Accordingly, the preferred embodiments of the invention as set forth herein are intended to be illustrative, not limiting. Various changes may be made without departing from the spirit and scope of this invention.

What is claimed is:

1. A method for detecting an extent of deterioration of a bill, comprising:

generating at least one transmitted light image and at least one reflected light image of the bill;

determining at least one disorder curve length for at least some of the at least one transmitted light image and at least some of the at least one reflected light image;

determining at least one evaluation factor for at least some of the at least one transmitted light image and at least one evaluation factor for at least some of the at least one reflected light image based on the determined disorder curve lengths; and determining the extent of deterioration of the bill based on at least some of the determined evaluation factors.

2. The method of claim 1, wherein determining the at least one disorder curve length for at least some of the at least one transmitted light image and at least some of the at least one reflected light image comprises, for each such transmitted light image and each such reflected light image:

dividing that image into a plurality of blocks;

determining at least one disorder curve length for at least some of the plurality of blocks;

determining at least one evaluation value for at least some of the plurality of blocks based on at least some of the determined at least one disorder curve length; and determining at least one of either a maximum evaluation value or a minimum evaluation value for that image from the at least one evaluation value determined for at least some of the plurality of blocks.

3. The method of claim 2, wherein determining the at least one evaluation value comprises, for each of at least some of the at least one determined disorder curve length, comparing that disorder curve length to a corresponding disorder curve length of a corresponding block of a corresponding reference image.

4. The method of claim 3, wherein comparing each such disorder curve length for a block to the corresponding disorder curve length of the corresponding block of the corresponding reference image comprises dividing that disorder curve length by the corresponding reference disorder curve length.

5. The method of claim 3, wherein comparing each such disorder curve length for a block to the corresponding disorder curve length of the corresponding block of the corresponding reference image comprises subtracting the corresponding reference disorder curve length from the disorder curve length for that block;

determining at least one disorder curve length for at least some of the plurality of blocks.

6. The method of claim 2, wherein determining at least one disorder curve length for at least some of the plurality of blocks comprises determining, for each such block, at least one of a horizontal disorder curve length and a vertical disorder curve length.

7. The method of claim 1, wherein determining the extent of deterioration comprises plotting the determined evaluation values on a predetermined evaluation map.

8. A system for determining an extent of deterioration of a bill from at least one transmitted light image and at least one reflected light image of the bill, comprising:

a controller;

a disorder curve length determiner circuit that determines at least one disorder curve length for at least some of the of the at least one reflected light image and at least some of the at least one transmitted light image;

a memory that stores a plurality of reference disorder curve lengths corresponding to the at least one determined disorder curve length for the at least one transmitted light image and the at least one reflected light image;

a comparator circuit that compares the reference disorder curve lengths to the corresponding determined disorder curve lengths to generate at least one transmitted light evaluation factor and at least one reflected light evaluation factor, and that determines at least one of a maximum evaluation factor and a minimum evaluation factor for at least some of the at least one transmitted light image and at least one of either a maximum or a minimum evaluation factor for at least some of the at least one reflected light image; and an evaluation factor analyzer circuit that determines an extent of deterioration of the bill based on at least one of the maximum evaluation factor and the minimum evaluation factor for at least some of the at least one transmitted light image and at least some of the at least one reflected light image.

* * * * *